United States Patent [19]

Yagihara et al.

[11] 4,409,320
[45] Oct. 11, 1983

[54] SILVER HALIDE COLOR PHOTOGRAPHIC LIGHT-SENSITIVE MATERIAL

[75] Inventors: Morio Yagihara; Tsumoru Hirano; Keiji Mihayashi; Takashi Ozawa, all of Kanagawa, Japan

[73] Assignee: Fuji Photo Film Co., Ltd., Kanagawa, Japan

[21] Appl. No.: 377,271

[22] Filed: May 10, 1982

[30] Foreign Application Priority Data

May 8, 1981 [JP] Japan ................... 56-68979

[51] Int. Cl.³ .................. G03C 7/00; G03C 1/40
[52] U.S. Cl. ................... 430/381; 430/372; 430/386; 430/548; 430/554
[58] Field of Search ............ 430/372, 381, 548, 554, 430/630, 386

[56] References Cited

U.S. PATENT DOCUMENTS

| | | | |
|---|---|---|---|
| 3,163,625 | 12/1964 | Firestine et al. | 430/627 |
| 3,926,436 | 12/1975 | Monbaliu et al. | 430/554 |
| 4,080,211 | 3/1978 | Van Paesschen et al. | 430/548 |
| 4,128,427 | 12/1978 | Monbaliu et al. | 430/548 |

Primary Examiner—J. Travis Brown
Attorney, Agent, or Firm—Sughrue, Mion, Zinn, Macpeak and Seas

[57] ABSTRACT

A silver halide color photographic light-sensitive material comprising a support having thereon a silver halide emulsion layer containing a magenta color image forming polymer coupler latex which is capable of forming a dye upon coupling with an oxidation product of an aromatic primary amine developing agent and which is a polymer or copolymer having a repeating unit derived from a monomer represented by the following general formula (I)

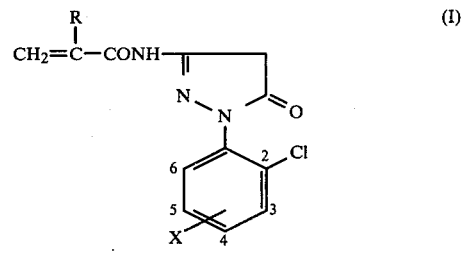

wherein R represents a hydrogen atom, a lower alkyl group containing from 1 to 4 carbon atoms or a chlorine atom; and X represents a halogen atom, an acylamino group, a carbamoyl group, a sulfonamido group, a sulfamoyl group, a cyano group or an alkoxycarbonyl group and which is present at the 4-position or 5-position of the phenyl group. The magenta color image forming polymer coupler latex has a good color forming property and is capable of forming a dye with a high yield and without formation of undesired stains and fogs, and the silver halide color photographic light-sensitive material containing the magenta color image forming polymer coupler latex has good film strength and a reduced layer thickness and provides a stable magenta image having an improved sharpness and a good fastness to light, heat, and humidity. A method of forming a color image using the silver halide color photographic light-sensitive material is also described.

16 Claims, No Drawings

SILVER HALIDE COLOR PHOTOGRAPHIC LIGHT-SENSITIVE MATERIAL

BACKGROUND OF THE INVENTION

The present invention relates to a silver halide color photographic light-sensitive material containing a novel magenta color image forming polymer coupler latex capable of coupling with an oxidation product of an aromatic primary amine developing agent.

It is well known that for the color development of a silver halide photographic light-sensitive material, after exposure, an oxidized aromatic primary amine developing agent can be reacted with a dye forming coupler to obtain a color image.

It is also known that, for the color development of a silver halide color photographic material, an oxidized aromatic primary amine color developing agent can be reacted with a coupler to form a dye such as an indophenol, an indoaniline, an indamine, an azomethine, a phenoxazine, a phenazine, and the like, thus forming a color image. In this procedure, the subtractive color process is ordinarily used for color reproduction, and silver halide emulsions which are selectively sensitive to blue, green, and red light, and yellow, magenta, and cyan color image formers, which are respectively the complementary colors of blue, green, and red, are employed. For example, a coupler of the acylacetanilide or benzoylmethane type is used for forming a yellow color image; a coupler of the pyrazolone, pyrazolobenzimidazole, cyanoacetophenone or indazolone type is generally used for forming a magenta color image; and a phenolic coupler, such as a phenol and a naphthol, is generally used for forming a cyan color image.

Color couplers must satisfy various requirements. For example, it is necessary that they have a good spectral property and provide a dye image having excellent stability to light, temperature, and humidity for a long period of time upon color development.

It is also required in a multilayer color photographic light-sensitive material that each coupler is fixed in a layer separated from each other in order to reduce color mixing and improve color reproduction. Many methods for rendering a coupler diffusion-resistant are known. One method is to introduce a long chain aliphatic group into a coupler molecule in order to prevent diffusion. Couplers according to such a method require a step of addition to an aqueous gelatin solution by solubilizing in alkali, or a step of dispersing in an aqueous gelatin solution by dissolving in a high boiling organic solvent, since the couplers are immiscible with an aqueous gelatin solution. Such color couplers may cause crystal formation in a photographic emulsion. Furthermore, when using a high boiling organic solvent, a large amount of gelatin must be employed since the high boiling organic solvent makes an emulsion layer soft. Consequently, this increases the thickness of the material even though it is desirable to reduce the thickness of the emulsion layer.

Another method for rendering a coupler diffusion-resistant is to utilize a polymer coupler latex obtained by polymerization of a monomeric coupler. An example of a method of adding a polymer coupler in a latex form to a hydrophilic colloid composition is a method in which a latex prepared by an emulsion polymerization method is directly added to a gelatino silver halide emulsion and a method in which an oleophilic polymer coupler obtained by polymerization of a monomeric coupler is dispersed in a latex form in an aqueous gelatin solution. Some examples of the former emulsion polymerization methods include an emulsion polymerization method in an aqueous gelatin phase as described in U.S. Pat. No. 3,370,952 and an emulsion polymerization method in water as described in U.S. Pat. No. 4,080,211. An example of the latter method in which a lipophilic polymer coupler is dispersed in a latex form in gelatin is described in U.S. Pat. No. 3,451,820. The method of adding a polymer coupler in a latex form to a hydrophilic colloid composition has many advantages in comparison with other methods. For example, the deterioration of strength of the film formed is small, because the hydrophobic substance is in a latex form. Also, since the latex can contain coupler monomers in a high concentration, it is easy to incorporate couplers in a high concentration into a photographic emulsion, and the increase of viscosity is small. Furthermore, color mixing is prevented, since a polymer coupler is completely immobilized and the crystallization of couplers in the emulsion layer is small. In particular, when the polymer coupler latex prepared by an emulsion polymerization method is used, the step of adding the coupler to a coating solution can be simpified, since the use of a high boiling organic solvent or an alkali is not necessary and a special dispersing method is not required. Moreover, the thickness of the layer can be reduced, since an organic solvent is not contained therein.

With respect to the addition of these polymer couplers in a latex form to a gelatino silver halide emulsion, there are described, for example, 4-equivalent magenta polymer coupler latexes and methods of preparation thereof in U.S. Pat. No. 4,080,211, British Pat. No. 1,247,688, and U.S. Pat. No. 3,451,820, copolymer latexes with a competing coupler in West German Pat. No. 2,725,591, and U.S. Pat. No. 3,926,436 and cyan polymer coupler latexes in U.S. Pat. No. 3,767,412.

However, these polymer coupler latexes have a number of problems to be dissolved in addition to the many advantages described above, and thus it has been desired to overcome these problems. The problems include the following:

1. The absorption peak of the magenta dye is broadened, and thus the color reproducibility is inferior.
2. The rate of the coupling reaction is poor, and thus the density of dye formed is very low.
3. The light fastness of the magenta color image is very poor.
4. Undesirable fog is readily formed upon color development.
5. The fastness to humidity and heat of the color image is poor.
6. The solubility of the coupler monomer is low, and the polymerizability thereof is very poor.

More particularly, they have major disadvantages in color reproducibility, coupling reactivity, light fastness of magenta color image, stability of polymer coupler latex in a film during storage, and the polymerizability of the coupler monomer. With respect to the coupling reactivity, no improvement is obtained by using the 2-equivalent magenta polymer coupler latex described in West German Pat. No. 2,725,591 and U.S. Pat. No. 3,926,436. This suggests that there are great differences in photographic properties between conventional couplers and polymer couplers.

SUMMARY OF THE INVENTION

Therefore, an object of the present invention is to provide a novel magenta color image forming polymer coupler latex in which the disadvantages described above are eliminated, and which is free from the formation of undesirable fog and stain.

Another object of the present invention is to provide a novel magenta color image forming polymer coupler latex which has an excellent color forming property.

Another object of the present invention is to provide a novel magenta color image forming polymer coupler latex which provides an excellent color reproducibility.

Still another object of the present invention is to provide a color photographic light-sensitive material that forms a color image fast to light, heat, and humidity in a color photograph after development processing.

A further object of the present invention is to provide a color photographic light-sensitive material having good film strength.

A further object of the present invention is to provide a color photographic light-sensitive material having a reduced layer thickness and an improved sharpness.

A still further object of the present invention is to provide a method of forming a magenta color image by development of a silver halide emulsion in the presence of a novel magenta dye forming polymer coupler latex.

A still further object of the present invention is to provide a silver halide color photographic light-sensitive material containing a novel magenta dye forming polymer coupler latex, a photographic processing method or an image forming method for using the material.

Other objects of the present invention will be apparent from the following detailed description and examples.

As a result of extensive investigations, it has now been found that these objects of the present invention are accomplished by the use of a magenta color image forming polymer coupler latex which is a polymer or copolymer having a repeating unit derived from a monomer represented by the following general formula (I)

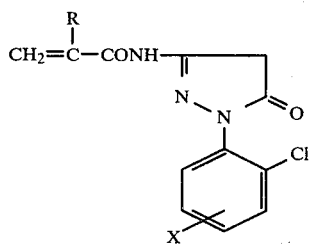

(I)

wherein R represents a hydrogen atom, a lower alkyl group containing from 1 to 4 carbon atoms or a chlorine atom; and X represents a halogen atom, an acylamino group, a carbamoyl group, a sulfonyl group, a sulfonamido group, a sulfamoyl group, a cyano group or an alkoxycarbonyl group and which is present at the 4-position or 5-position of the phenyl group.

In more detail, the objects of the invention can be accomplished with a color photographic light-sensitive material comprising a support having thereon at least one silver halide emulsion layer containing a magenta color image forming polymer coupler latex which is a novel homopolymer having a repeating unit represented by the general formula (II) described below, or a novel copolymer of the repeating unit described below and a non-color forming unit which does not couple with the oxidation product of an aromatic primary amine developing agent.

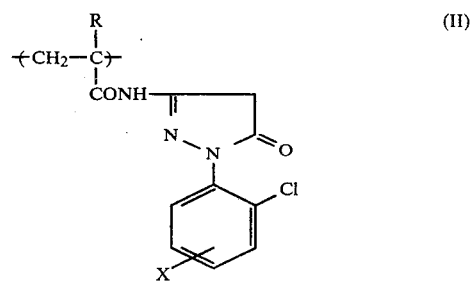

(II)

wherein R and X have the same meanings as defined in the general formula (I) above.

DETAILED DESCRIPTION OF THE INVENTION

The novel magenta color image forming polymer coupler latex according to the present invention includes a polymer having a repeating unit derived from a monomer coupler represented by the general formula (I), and a copolymer of the repeating unit according to formula (II) and at least one non-color forming unit containing at least one ethylene group which does not have an ability of oxidative coupling with an aromatic primary amine developing agent.

In the above-described formula (I), R represents a hydrogen atom, a lower alkyl group having from 1 to 4 carbon atoms, or a chlorine atom; X, which is present at the 4-position or 5-position of the phenyl group, represents a halogen atom (for example, a fluorine atom, a chlorine atom, a bromine atom, etc.), an acylamino group (for example, an acetylamino group, etc.), a carbamoyl group (for example, a methylcarbamoyl group, a dimethylcarbamoyl group, etc.), a sulfonamido group (for example, a methanesulfonamido group, etc.), a sulfamoyl group (for example, an ethylsulfamoyl group, a dimethylsulfamoyl group, etc.), a cyano group, or an alkoxycarbonyl group (for example, a methoxycarbonyl group, an ethoxycarbonyl group, etc.). Of these substituents represented by X, a halogen atom is particularly preferred in view of color reproducibility, color forming property and stability.

Examples of the non-color forming monomer which does not couple with the oxidation product of an aromatic primary amine developing agent include an ester, preferably a $C_1$-$C_8$ alkyl ester and an amide, derived from an acrylic acid, for example, an acrylic acid, an α-chloroacrylic acid, an α-alkylacrylic acid such as a methacrylic acid, for example, acrylamide, methacrylamide, t-butylacrylamide, methyl acrylate, ethyl acrylate, n-propyl acrylate, n-butyl acrylate, 2-ethylhexyl acrylate, n-hexyl acrylate, octyl methacrylate, lauryl methacrylate, methylenebisacrylamide, etc., a vinyl ester, for example, vinyl acetate, vinyl propionate, vinyl laurate, etc., acrylonitrile, methacrylonitrile, an aromatic vinyl compound, for example, styrene and a derivative thereof, for example, vinyl toluene, divinyl benzene, vinyl acetophenone, sulfostyrene, etc., itaconic acid, citraconic acid, crotonic acid, vinylidene chloride, a vinyl alkyl ether, for example, vinyl ethyl ether, an ester of maleic acid, N-vinyl-2-pyrrolidone, N-vinylpyridine, 2- or 4-vinylpyridine, etc.

Of these monomers, an ester of acrylic acid, an ester of methacrylic acid, an ester of maleic acid are particularly preferred.

Two or more comonomer compounds described above can be used together. For example, a combination of n-butyl acrylate and divinyl benzene, styrene and methacrylic acid, n-butyl acrylate and methacrylic acid, etc., can be used.

The ethylenically unsaturated monomer which is used to copolymerize with the monomer coupler represented by the above-described general formula (II) can be selected so that the copolymer to be formed possesses good physical properties and/or chemical properties, for example, solubility, compatibility with a binder such as gelatin in a photographic colloid composition, flexibility, heat stability, etc., as well known in the field of polymer color couplers.

The magenta polymer coupler latex used in the present invention can be prepared by an emulsion polymerization method as described above, or by dissolving an oleophilic polymer coupler obtained by polymerization of a monomer coupler in an organic solvent and then dispersing the solution in a latex form in an aqueous gelatin solution. With respect to the emulsion polymerization, the methods as described in U.S. Pat. Nos. 4,080,211 and 3,370,952 and with respect to the method in which an oleophilic polymer coupler is dispersed in a latex form in an aqueous gelatin solution, the method as described in U.S. Pat. No. 3,451,820 can be employed, respectively. These methods can be applied to preparation of homopolymers and preparation of copolymers. In the latter case, a non-color forming comonomer is preferably a liquid comonomer which may act, in the case of the emulsion polymerization, as a solvent for a monomer which is normally solid.

Free radical polymerization of an ethylenically unsaturated solid monomer is initiated with the addition to the monomer molecule of a free radical which is formed by thermal decomposition of a chemical initiator, an action of a reducing agent to an oxidative compound (a redox initiator) or a physical action, for example, irradiation of ultraviolet rays or other high energy radiations, high frequencies, etc.

Examples of the chemical initiators commonly used include a water-soluble initiator, for example, a persulfate (such as ammonium persulfate, potassium persulfate, etc.), hydrogen peroxide, 4,4'-azobis(4-cyanovaleric acid), etc., and a water-insoluble initiator, for example, azoisobutyronitrile, benzoyl peroxide, chlorobenzoyl peroxide, and other compounds. Examples of the redox initiators usually used include hydrogen peroxide-iron (II) salt, potassium persulfate-potassium hydrogensulfate, cerium salt-alcohol, etc. Specific examples and functions of the initiators are described in F. A. Bovey, *Emulsion Polymerization*, pages 59–93, (Interscience Publisher Inc., New York (1955)).

As an emulsifier which can be used in the emulsion polymerization, a compound having surface activity is used. Preferred examples include soap, a sulfonate, a sulfate, a cationic compound, an amphoteric compound and a high molecular weight protective colloid. Specific examples and functions of the emulsifiers are described in *Belgische Chemische Industrie*, Vol. 28, pages 16–20 (1963).

On the other hand, an organic solvent which is used for dissolving an oleophilic polymer coupler in the case where the oleophilic polymer coupler is dispersed in a latex form in an aqueous gelatin solution is removed from the mixture before coating of the dispersion solution or by vaporization during drying of the dispersion solution coated, although the latter is less preferable. With respect to removing the solvent, a method in which the solvent is removed by washing a gelatin noodle with water is applied when the solvent is water-soluble to some extent, or a spray drying method, a vacuum urging method or a steam purging method can be employed for removing the solvent.

Examples of the organic solvents which can be removed include, for example, an ester (for example, a lower alkyl ester, etc.), a lower alkyl ether, ketone, halogenated hydrocarbon (for example, methylene chloride, trichloroethylene, a fluorinated hydrocarbon, etc.), an alcohol (for example, an alcohol between n-butyl alcohol and octyl alcohol, etc.), and a mixture thereof.

Any type of dispersing agent can be used in the dispersion of the oleophilic polymer coupler. Ionic surface active agents, and particularly anionic surface active agents are preferred. Amphoteric surface active agents such as C-cetyl betaine, an N-alkylaminopropionate, an N-alkyliminodipropionate, etc., can also be used.

In order to increase the dispersion stability, control the color hue of a dye formed from a polymer coupler latex dispersed and the oxidation product of an aromatic primary amine developing agent and improve the bending property of the emulsion coated, a permanent solvent, that is, a water-immiscible organic solvent having a high boiling point (i.e., above 200° C.), may be added in a small amount (i.e., not more than 50% by weight based on the polymer coupler). The concentration of the permanent solvent must be at such a low level that the copolymer is plasticized while it is maintained in solid particle form. Furthermore, it is desirable to use the permanent solvent in a relatively low concentration in order to reduce the thickness of a final emulsion layer as much as possible to obtain good sharpness.

It is desirable if the ratio of the color forming portion in the polymer coupler latex is usually from 5 to 80% by weight. Particularly, a ratio from 20 to 70% by weight is preferred in view of color reproducibility, color forming property and stability. In this case, an equivalent molecular weight, that is, a gram number of the polymer containing 1 mol of a coupler monomer is preferably from about 250 to 3,000, but it is not limited thereto.

Preferred specific examples of the coupler monomers used in the present invention are set forth below, but the present invention is not to be construed as being limited thereto.

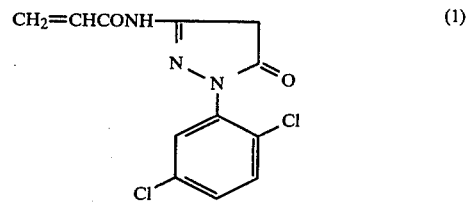

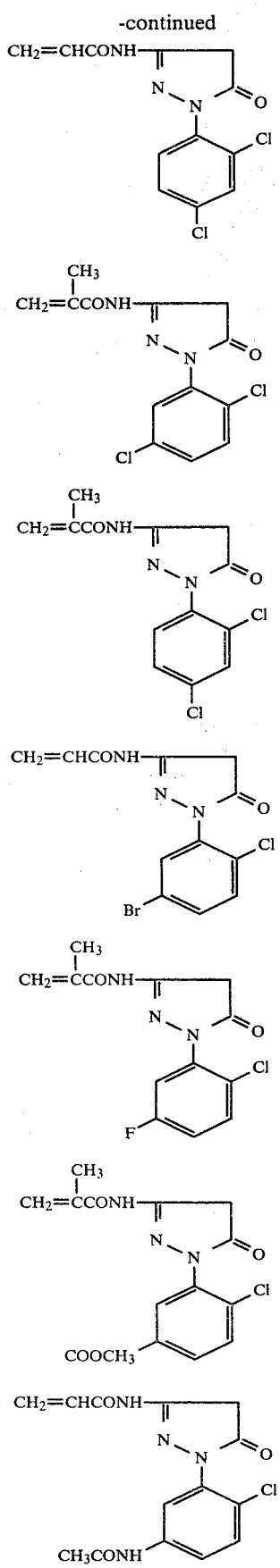

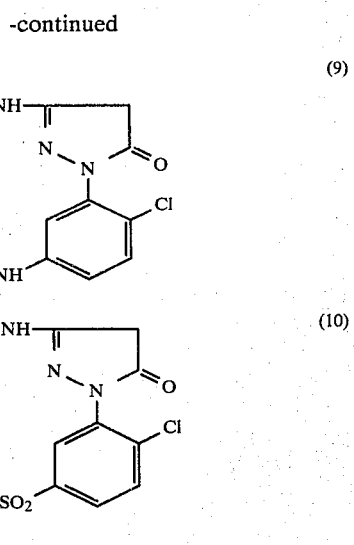

The monomeric coupler represented by the general formula (I) can be synthesized by reacting an acid halide of acrylic acid or an α-substituted acrylic acid, for example, acryloyl chloride, methacryloyl chloride, etc., with an appropriate 3-amino-2-pyrazolin-5-one compound as described in U.S. Pat. Nos. 3,325,482, 1,247,688, 3,163,625 and 3,356,686. Further, a 3-acryloylamino compound can be synthesized by dehydrogenchlorination with a base of a 3-(β-halopropanoylamino) compound which is obtained by reacting a β-halopropionyl chloride with a 3-amino-2-pyrazolin-5-one compound as shown in the synthesis examples described hereinafter.

The 3-amino-2-pyrazolin-5-one compound used can be synthesized by a ring-forming reaction of an appropriate aromatic hydrazine with β-amino-β-ethoxypropionic acid as described in U.S. Pat. No. 2,376,380, British Pat. Nos. 1,069,563, 1,166,035, 1,190,914 and 1,269,355, or by a reaction of an aromatic hydrazine with an ester of β-ethoxy-β-imino propionic acid as described in *J. Amer. Chem. Soc.*, Vol. 66, pages 1851 to 1855 (1944).

Typical synthesis examples of the compounds used in the present invention are set forth below.

A. Monomer Compounds

SYNTHESIS EXAMPLE 1

Synthesis of 1-(2,5-dichlorophenyl)-3-methacryloylamino-2-pyrazolin-5-one [Coupler Monomer (3)]

30 g (0.12 mol) of 3-amino-1-(2,5-dichlorophenyl)-2-pyrazolin-5-one was dissolved in 250 ml of tetrahydrofuran to which were added 21 ml (0.27 mol) of pyridine and 2.5 ml of nitrobenzene. To the mixture there was further added dropwise 28.2 g (0.27 mol) of methacryloyl chloride while cooling with ice and the mixture was stirred for about 30 minutes. After adding 250 ml of water, the mixture was extracted with ethyl acetate and the extract was dried with anhydrous sodium sulfate. After distilling off the solvent at from 20° C. to 30° C. under reduced pressure, the residual oily product was dissolved in a mixture of 360 ml of water and 200 ml of ethanol, to which was then added dropwise an aqueous solution containing 14.8 g (0.37 mol) of sodium hydroxide dissolved in 50 ml of water at room temperature. After stirring for 30 minutes, acetic acid was added to the mixture for neutralization and the crystals thus deposited were collected by filtration. By recrystallization from acetonitrile 19.5 g (52% yield) of Coupler Monomer (3) was obtained.

Melting Point: 179° to 180° C.
Elemental Analysis for $C_{13}H_{11}N_3O_2Cl_2$

|  | H | C | N |
|---|---|---|---|
| Calculated (%): | 3.55 | 49.06 | 13.46 |
| Found (%): | 3.54 | 49.33 | 13.53 |

SYNTHESIS EXAMPLE 2

Synthesis of 1-(2,4-dichlorophenyl)-3-methacryloylamino-2-pyrazolin-5-one [Coupler Monomer (4)]

30 g (0.12 mol) of 3-amino-1-(2,4-dichlorophenyl)-2-pyrazolin-5-one was dissolved in 250 ml of tetrahydrofuran to which were added 21 ml (0.27 mol) of pyridine and 2.5 ml of nitrobenzene. To the mixture was added dropwise 28.2 g (0.27 mol) of methacryloyl chloride while cooling with ice and the mixture was additionally stirred for about 30 minutes. After adding 250 ml of water, the mixture was extracted with ethyl acetate, and the extracted solution was dried with anhydrous sodium sulfate. After distilling off the solvent at from 20° C. to 30° C. under reduced pressure, the residual oily product was dissolved in a mixture of 360 ml of water and 200 ml of ethanol, to which was then added an aqueous solution containing 14.8 g (0.37 mol) of sodium hydroxide dissolved in 50 ml of water at room temperature. After stirring for 30 minutes, acetic acid was added to the mixture for neutralization and the crystals thus deposited were collected by filtration. By recrystallization from acetonitrile 23.1 g (62% yield) of Coupler Monomer (4) was obtained.

Melting Point: 151° to 153° C.
Elemental Analysis for $C_{13}H_{11}N_3O_2Cl_2$

|  | H | C | N |
|---|---|---|---|
| Calculated (%): | 3.55 | 49.06 | 13.46 |
| Found (%): | 3.31 | 49.33 | 13.29 |

SYNTHESIS EXAMPLE 3

Synthesis of 1-(2,5-dichlorophenyl)-3-acryloylamino-2-pyrazolin-5-one [Coupler Monomer (1)]

48.8 g (0.2 mol) of 3-amino-1-(2,5-dichlorophenyl)-2-pyrazolin-5-one was added to 300 ml of acetonitrile to which was added dropwise 30.4 g (0.24 mol) of β-chloropropionyl chloride while heating at from 60° C. to 70° C. with stirring. After refluxing by heating for about 1 hour, the mixture was cooled to about 25° C. and the crystals thus deposited were collected by filtration to obtain 48 g (80% yield) of 1-(2,5-dichlorophenyl)-3-(β-chloropropanoylamino)-2-pyrazolin-5-one.

Then, 33.5 g (0.1 mol) of the β-chloropropanoylamino compound thus obtained was added to 150 ml of methanol and to the solution was added dropwise a solution containing 16.8 g (0.3 mol) of potassium hydroxide dissolved in 150 ml of methanol while cooling with ice. After stirring for about 30 minutes, acetic acid was added to the mixture for neutralization and 500 ml of water was added to the mixture. The crystals thus deposited were collected by filtration and recrystallized from acetonitrile to obtain 22.5 g (75% yield) of Coupler Monomer (1).

Melting Point: 201° to 202° C.
Elemental Analysis for $C_{12}H_9N_3O_2Cl_2$

|  | H | C | N |
|---|---|---|---|
| Calculated (%) | 3.04 | 48.34 | 14.09 |
| Found (%) | 3.09 | 48.33 | 14.30 |

SYNTHESIS EXAMPLE 4

Synthesis of 1-(2,4-dichlorophenyl)-3-acryloylamino-2-pyrazolin-5-one [Coupler Monomer (2)]

30 g (0.12 mol) of 3-amino-1-(2,4-dichlorophenyl)-2-pyrazolin-5-one was added to 150 ml of acetonitrile to which was added dropwise 17.8 g (0.14 mol) of β-chloropropionyl chloride while heating at from 60° C. to 70° C. with stirring. After refluxing by heating for about 1 hour, the mixture was cooled to about 25° C. and the crystals thus deposited were collected by filtration to obtain 30 g (83% yield) of 1-(2,4-dichlorophenyl)-3-(β-chloropropanoylamino)-2-pyrazolin-5-one.

Then, 17 g (0.5 mol) of the β-chloropropanoylamino compound thus obtained was added to 75 ml of methanol and to the solution was added dropwise a solution containing 8.4 g (0.15 mol) potassium hydroxide dissolved in 75 ml of methanol while coupling with ice. After stirring for about 30 minutes, acetic acid was added to the mixture for neutralization and 250 ml of water was added to the mixture. The crystals thus deposited were collected by filtration and recrystallized from acetonitrile to obtain 24.1 g (80% yield) of Coupler Monomer (2).

Melting Point: 215° to 217° C.
Elemental Analysis for $C_{12}H_9N_3O_2Cl_2$

|  | H | C | N |
|---|---|---|---|
| Calculated (%): | 3.04 | 48.34 | 14.09 |
| Found (%): | 3.14 | 48.43 | 14.31 |

B. Polymer Compounds

SYNTHESIS EXAMPLE 5

Copolymer latex of 1-(2,5-dichlorophenyl)-3-acryloylamino-2-pyrazolin-5-one [Coupler Monomer (1)] and n-butyl acrylate [Polymer Coupler Latex (A)]

2 l of an aqueous solution containing 2 g of sodium salt of oleyl methyl tauride dissolved was stirred and heated to 95° C. while gradually introducing nitrogen gas through the solution. To the mixture was added 40 ml of an aqueous solution containing 280 mg of potassium persulfate dissolved. 20 g of n-butyl acrylate and 5 g of Coupler Monomer (1) were dissolved by heating in 400 ml of ethanol and the resulting solution was added to the above-described aqueous solution at an interval of about 30 minutes while preventing the deposition of crystals. After the completion of the addition, the mixture was heated at from 85° C. to 95° C. with stirring for 45 minutes, to which was then added 40 ml of an aqueous solution containing 120 mg of potassium persulfate dissolved. After being reacted for 1 hour, the ethanol and the n-butyl acrylate not reacted were distilled off as an azeotropic mixture with water. The latex thus-formed was cooled, pH of which was adjusted to 6.0 with a 1 N sodium hydroxide solution and filtered. The concentration of the polymer in the latex was 10.35% and it was found that the copolymer synthesized contained 47.2% of 1-(2,5-dichlorophenyl)-3-(acryloylamino-2-pyrazolin-5-one as the result of nitrogen analysis.

SYNTHESIS EXAMPLE 6

Copolymer latex of 1-(2,5-dichlorophenyl)-3-(methacryloylamino-2-pyrazolin-5-one [Coupler Monomer (3)] and n-butyl acrylate [Polymer Coupler latex (B)]

2 l of an aqueous solution containing 2 g of sodium salt of oleyl methyl tauride dissolved was stirred and heated to 95° C. while gradually introducing nitrogen gas through the solution. To the mixture was added 40 ml of an aqueous solution containing 280 mg of potassium persulfate dissolved. 20 g of n-butyl acrylate and 20 g of Coupler Monomer (3) were dissolved by heating in 400 ml of ethanol and the resulting solution was added to the above-described aqueous solution at an interval of about 30 minutes while preventing the deposition of crystals. After the completion of the addition, the mixture was heated at from 85° C. to 95° C. with stirring for 45 minutes, to which was then added 40 ml of an aqueous solution containing 120 mg of potassium persulfate dissolved. After being reacted for 1 hour, the ethanol and the n-butyl acrylate not reacted were distilled off as an azeotropic mixture with water. The latex thus-formed was cooled, pH of which was adjusted to 6.0 with a 1 N sodium hydroxide solution and filtered. The concentration of the polymer in the latex was 10.51% and it was found that the copolymer synthesized contained 47.6% of 1-(2,5-dichlorophenyl)-3-methacryloylamino-2-pyrazolin-5-one as the result of nitrogen analysis.

SYNTHESIS EXAMPLE 7

Copolymer latex of 1-(2,5-dichlorophenyl)-3-methacryloylamino-2-pyrazolin-5-one [Coupler Monomer (3)] and n-butyl acrylate [Polymer Coupler Latex (C)]

270 ml of an aqueous solution containing 1.54 g of sodium salt of oleyl methyl tauride dissolved was stirred and heated to 95° C. while gradually introducing nitrogen gas through the solution. To the mixture were added 20 ml of an aqueous solution containing 28 mg of potassium persulfate dissolved, and then 2.8 g of n-butyl acrylate. The mixture was polymerized by heating at from 85° C. to 95° C. with stirring for about 1 hour to prepare Latex (b). Then, to Latex (b) were added 14 g of Coupler Monomer (3), 100 ml of methanol and 10 ml of a methanol solution containing 14 g of n-butyl acrylate dissolved. To the mixture was then added 50 ml of an aqueous solution containing 196 mg of potassium persulfate dissolved and the mixture was polymerized by heating with stirring. After being reacted for 1 hour, 30 ml of an aqueous solution containing 84 mg of potassium persulfate was further added to the mixture and the mixture was continuously reacted for 1.5 hours. The methanol and the n-butyl acrylate not reacted were distilled off as an azeotropic mixture with water. The latex thus-formed was cooled, pH of which was adjusted to 6.0 with a 1 N sodium hydroxide solution and filtered. The concentration of the polymer in the latex was 10.2% and it was found that the copolymer synthesized contained 43.5% of 1-(2,5-dichlorophenyl)-3-methacryloylamino-2-pyrazolin-5-one as the result of nitrogen analysis.

SYNTHESIS EXAMPLE 8

Copolymer latex of 1-(2,5-dichlorophenyl)-3-methacryloylamino-2-pyrazolin-5-one [Coupler Monomer (3)] and n-butyl acrylate [Polymer Coupler Latex (D)]

180 ml of an aqueous solution containing 3.5 g of sodium salt of oleyl methyl tauride dissolved was stirred and heated to 95° C. while gradually introducing nitrogen gas through the solution. To the mixture was added 20 ml of an aqueous solution containing 240 mg of potassium persulfate dissolved. 60 g of n-butyl acrylate and 10 g of Coupler Monomer (3) were dissolved by heating at 140° C. and the resulting solution was added to the above-described aqueous solution while preventing the deposition of crystals. After the completion of the addition, the mixture was heated at from 85° C. to 95° C. with stirring for 45 minutes, to which was then added 10 ml of an aqueous solution containing 120 mg of potassium persulfate dissolved. After being reacted for 1 hour, n-butyl acrylate not reacted was distilled off as an azeotropic mixture with water. The latex thus-formed was cooled, and filtered. The concentration of the polymer in the latex was 26.4% and it was found that the copolymer synthesized contained 18.5% of 1-(2,5-dichlorophenyl)-3-methacryloylamino-2-pyrazolin-5-one as the result of nitrogen analysis.

SYNTHESIS EXAMPLE 9

Copolymer latex of 1-(2,5-dichlorophenyl)-3-methacryloylamino-2-pyrazolin-5-one [Coupler Monomer (3)] and ethyl acrylate [Polymer Coupler Latex (E)]

2 l of an aqueous solution containing 2 g of sodium salt of oleyl methyl tauride was stirred and heated to 95° C. while gradually introducing nitrogen gas through the solution. To the mixture was added 40 ml of an aqueous solution containing 280 mg of potassium persulfate dissolved. 20 g of ethyl acrylate and 20 g of Coupler Monomer (3) were dissolved by heating in 400 ml of ethanol and the resulting solution was added to the above-described aqueous solution at an interval of about 30 minutes while preventing the deposition of crystals. After the completion of the addition, the mixture was heated at from 85° C. to 95° C. with stirring for 45 minutes, to which was then added 40 ml of an aqueous solution containing 120 mg of potassium persulfate dissolved. After being reacted for 1 hour, the ethanol and the ethyl acrylate not reacted were distilled off as an azeotropic mixture with water. The latex thus-formed was cooled, pH of which was adjusted to 6.0 with a 1 N sodium hydroxide solution and filtered. The concentration of the polymer in the latex was 11.03% and it was found that the copolymer synthesized contained 51.3% of 1-(2,5-dichlorophenyl)-3-methacryloylamino-2-pyrazolin-5-one as the result of nitrogen analysis.

SYNTHESIS EXAMPLE 10

Copolymer latex of 1-(2,5-dichlorophenyl)-3-methacryloylamino-2-pyrazolin-5-one [Coupler Monomer (3)] and ethyl acrylate [Polymer Coupler Latex (F)]

A 270 ml of an aqueous solution containing 1.54 g of sodium salt of oleyl methyl tauride dissolved was stirred and heated to 95° C. while gradually introducing nitrogen gas through the solution. To the mixture were added 20 ml of an aqueous solution containing 28 mg of potassium persulfate dissolved, and then 2.8 g of ethyl acrylate. The mixture was polymerized by heating at from 85° C. to 95° C. with stirring for about 1 hour to prepare Latex (a). Then, to Latex (a) were added 14 g of Coupler Monomer (3), 100 ml of ethanol and 10 ml of an ethanol solution containing 14 g of ethyl acrylate dissolved. To the mixture was then added 50 ml of an aqueous solution containing 196 mg of potassium persulfate dissolved and the mixture was polymerized by heating at from 85° C. to 95° C. with stirring. After being reacted for 1 hour, 30 ml of an aqueous solution containing 84 mg of potassium persulfate was further added to the mixture and the mixture was continued to react for 1.5 hours. The ethanol and the ethyl acrylate not reacted were distilled off as an azeotropic mixture with water. The latex thus-formed was cooled, pH of which was adjusted to 6.0 with a 1 N sodium hydroxide solution and filtered. A concentration of the polymer in the latex was 10.3% and it was found that the copolymer synthesized contained 43.7% of 1-(2,5-dichlorophenyl)-3-methacryloylamino-2-pyrazolin-5-one as the result of nitrogen analysis.

SYNTHESIS EXAMPLE 11

Synthesis of Oleophilic Polymer Coupler (1)

To a mixture of 20 g of Coupler Monomer (3), 20 g of n-butyl acrylate and 150 ml of dioxane was added 350 mg of azobisisobutyronitrile dissolved in 10 ml of dioxane while heating at 60° C. with stirring and the mixture was reacted for about 5 hours. The resulting mixture was then poured into 2 l of ice water and the solid thus deposited was collected by filtration and thoroughly washed with water. By drying the product, 38.4 g of the oleophilic polymer coupler was obtained. It was found that the oleophilic polymer coupler contained 55.1% of Coupler Monomer (3) in the copolymer synthesized as the result of nitrogen analysis.

Synthesis of Polymer Coupler Latex (A')

Two solutions (a) and (b) were prepared in the following manner.
Solution (a): 300 g of a 5% by weight aqueous solution of bone gelatin (pH of 5.6 at 35° C.) was heated to 32° C. and to which was added 12 ml of a 10% by weight aqueous solution of sodium lauryl sulfate.
Solution (b): 20 g of the oleophilic polymer coupler described above was dissolved in 60 g of ethyl acetate at 38° C.
Solution (b) was put into a mixer with explosion preventing equipment while stirring at a high speed to which was rapidly added solution (a). After stirring for 1 minute, the mixer was stopped and ethyl acetate was removed by distillation under a reduced pressure. Thus the oleophilic polymer coupler was dispersed in a diluted gelatin solution to prepare Polymer Coupler Latex (A').

SYNTHESIS EXAMPLE 12

Synthesis of Oleophilic Polymer Coupler (2)

To a mixture of 20 g of Coupler Monomer (9), 20 g of ethyl acrylate and 150 ml of tertiary butanol was added 350 mg of azobisisobutyronitrile dissolved in 10 ml of tertiary butanol while refluxing by heating with stirring and the mixture was refluxed for about 1 hour. The resulting mixture was then poured into 2 l of ice water and the solid thus deposited was collected by filtration and thoroughly washed with water. By drying the product, 35.2 g of the oleophilic polymer coupler was obtained. It was found that the oleophilic polymer coupler contained 51.3% of Coupler Monomer (9) in the copolymer synthesized as the result of nitrogen analysis.

Synthesis of Polymer Coupler Latex (B')

Polymer Coupler Latex (B') was prepared in the same procedure as in the above described Polymer Coupler Latex (A').

SYNTHESIS EXAMPLE 13

Synthesis of Oleophilic Polymer Coupler (3)

A mixture of 20 g of Coupler Monomer (4), 40 g of n-butyl acrylate and 200 ml of dioxane was heated to 60° C. with stirring under a nitrogen gas atmosphere, to which was added 520 mg of azobisisobutyronitrile dissolved in 10 ml of dioxane and the mixture was reacted for about 6 hours. The resulting mixture was then poured into 3.0 l of ice water and the solid thus deposited was collected by filtration and thoroughly washed with water. By drying the product, 55.3 g of the oleophilic polymer coupler was obtained. It was found that the oleophilic polymer coupler contained 33.7% of Coupler Monomer (4) in the copolymer synthesized as the result of nitrogen analysis.

Synthesis of Polymer Coupler Latex (C')

Two solutions (a) and (b) were prepared in the following manner.
Solution (a): 200 g of a 3.0% by weight aqueous solution of bone gelatin (pH of 5.6 at 35° C.) was heated to 38° C. and to which was added 16 ml of a 10% by weight aqueous solution of sodium lauryl sulfate.
Solution (b): 20 g of the oleophilic polymer coupler described above was dissolved in 200 ml of ethyl acetate at 38° C.
Solution (b) was put into a mixer with explosion preventing equipment while stirring at high speed and to which was rapidly added Solution (a). After stirring for 1 minute, the mixer was stopped and ethyl acetate was removed by distillation under a reduced pressure. Thus the oleophilic polymer coupler was dispersed in a diluted gelatin solution to prepare Polymer Coupler Latex (C').

SYNTHESIS EXAMPLES 13 TO 40

Using the above-described coupler monomers, the magenta polymer coupler latexes described below were prepared in the same manner as described for the copolymers in Synthesis Examples 5, 6 and 9 (Synthesis Method I) (also in the same manner as described in Synthesis Examples 7, 8 and 10) and in Synthesis Examples 11 and 12 (Synthesis Method II).

| Synthesis Example | Polymer Coupler Latex | Coupler Monomer | Amount (g) | Co-monomer*1 | Amount (g) | Coupler Monomer Unit in Polymer (%) |
|---|---|---|---|---|---|---|
| Synthesis Method I ||||||||
| 13 | (G) | (1) | 20 | BA | 60 | 23.6 |
| 14 | (H) | (1) | 15 | " | 10 | 58.4 |
| 15 | (I) | (1) | 20 | MA | 20 | 51.6 |
| 16 | (J) | (1) | 20 | EA | 20 | 53.7 |
| 17 | (K) | (2) | 20 | BA | 20 | 48.4 |
| 18 | (L) | (3) | 20 | " | 80 | 20.3 |
| 19 | (M) | (3) | 20 | " | 10 | 63.4 |
| 20 | (N) | (3) | 20 | EA | 30 | 42.3 |
| 21 | (O) | (3) | 15 | " | 10 | 59.9 |
| 22 | (P) | (3) | 20 | MA | 20 | 56.7 |
| 23 | (Q) | (3) | 20 | HA | 20 | 47.3 |
| 24 | (R) | (3) | 20 | OMA | 20 | 46.9 |
| 25 | (S) | (3) | 20 | St | 20 | 48.1 |
| 26 | (T) | (3) | 20 | BMA | 20 | 48.7 |
| 27 | (U) | (4) | 20 | MA | 20 | 55.4 |
| 28 | (V) | (4) | 20 | EA | 20 | 50.2 |
| 29 | (W) | (5) | 20 | BA | 20 | 49.3 |
| 30 | (X) | (7) | 20 | " | 20 | 48.1 |
| 31 | (Y) | (3) | 20 | MA / DVB | 20 / 0.4 | 48.3 |
| 32 | (Z) | (3) | 20 | BA / MAA | 20 / 2 | 45.3 |
| Synthesis Method II ||||||||
| 33 | (D') | (1) | 20 | BA | 40 | 35.1 |
| 34 | (E') | (2) | 20 | EA | 80 | 20.5 |
| 35 | (F') | (3) | 20 | EA | 40 | 33.6 |
| 36 | (G') | (3) | 20 | EA | 20 | 50.3 |
| 37 | (H') | (4) | 20 | BA | 20 | 52.4 |
| 38 | (I') | (5) | 20 | OA | 10 | 68.3 |
| 39 | (J') | (6) | 20 | OMA | 10 | 67.2 |
| 40 | (K') | (7) | 20 | MMA | 40 | 38.2 |

(*1)MA: Methyl Acrylate
EA: Ethyl Acrylate
BA: n-Butyl Acrylate
HA: n-Hexyl Acrylate
OA: n-Octyl Acrylate
MMA: Methyl Methacrylate
BMA: n-Butyl Methacrylate
OMA: n-Octyl Methacrylate
St: Styrene
MMA: Methacrylic Acid
DVB: Divinylbenzene The 4-equivalent magenta polymer coupler latexes according to the present invention can be used individually or as mixtures of two or more thereof.

The 4-equivalent magenta polymer coupler latexes according to the present invention can also be used together with a 4-equivalent magneta polymer coupler latex, such as those described in U.S. Pat. No. 4,080,211, British Pat. No. 1,247,688, etc.

Further, a dispersion which is prepared by dispersing a hydrophobic magenta color forming coupler, for example, a magenta coupler, as described in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, West German Pat. No. 1,810,464, West German Patent Application (OLS) Nos. 2,408,665, 2,417,945, 2,418,959 and 2,424,467, Japanese Patent Publication No. 6031/65, Japanese Patent Application (OPI) Nos. 20826/76, 58922/77, 129538/74, 74027/74, 159336/75, 42121/77, 74028/74, 60233/75, 26541/76 and 55122/78 (the term "OPI" as used herein refers to a "published unexamined Japanese patent application"), etc., in a hydrophilic colloid in a manner as described, for example, in U.S. Pat. Nos. 2,269,158, 2,272,191, 2,304,940, 2,311,020, 2,322,027, 2,360,289, 2,772,163, 2,801,170, 2,801,171 and 3,619,195, British Pat. No. 1,151,590, West German Pat. No. 1,143,707, etc., is loaded into the 4-equivalent magenta polymer coupler latex according to the present invention in a manner as described in Japanese Patent Application (OPI) No. 39853/76, etc., and the resulting latex can be used. It is also possible for the above-described hydrophobic magenta coupler to be loaded into the 4-equivalent magenta polymer coupler latex according to the present invention in a manner as described in Japanese Patent Application (OPI) Nos. 59942/76 and 32552/79, U.S. Pat. No. 4,199,363, etc., and the resulting latex can be used. The term "load" used herein refers to the state in which a hydrophobic magenta coupler is incorporated into the interior of a 4-equivalent magenta polymer coupler latex, or a state in which a hydrophobic magenta coupler is deposited on the surface of a 4-equivalent magenta polymer coupler latex. However, the mechanism by which the load occurs is not accurately known.

In order to satisfy the characteristics required of the photographic light-sensitive material, a dispersion which is prepared by dispersing a development inhibitor releasing (DIR) coupler as described, for example, in U.S. Pat. Nos. 3,148,062, 3,227,554, 3,733,201, 3,617,291, 3,703,375, 3,615,506, 3,265,506, 3,620,745, 3,632,345, 3,869,291, 3,642,485, 3,770,436 and 3,808,945, British Pat. Nos. 1,201,110 and 1,236,767, etc., in a hydrophilic colloid in a manner as described in U.S. Pat. Nos. 2,269,158, 2,272,191, 2,304,940, 2,311,020, 2,322,027, 2,360,289, 2,772,163, 2,801,170, 2,801,171 and 3,619,195, British Pat. No. 1,151,590, West German Pat. No. 1,143,707, etc., is loaded into the 4-equivalent magenta polymer coupler latex according to the present invention in a manner as described in Japanese Patent Application (OPI) No. 39853/76. The resulting latex can then be used, or the above-described DIR coupler is loaded into the 4-equivalent magenta polymer coupler latex in a manner as described in Japanese Patent Application (OPI) Nos. 59942/76 and 32552/79, U.S. Pat. No. 4,199,363, etc., and the resulting latex can then be used.

Furthermore, the 4-equivalent magenta polymer coupler latex according to the present invention can be used together with a DIR compound as described, for example, in West German Patent Application (OLS) Nos. 2,529,350, 2,448,063 and 2,610,546, U.S. Pat. Nos. 3,928,041, 3,958,993, 3,961,959, 4,049,455, 4,052,213, 3,379,529, 3,043,690, 3,364,022, 3,297,445 and 3,287,129.

Moreover, the 4-equivalent magenta polymer coupler latex according to the present invention can be used in combination with a colored magenta coupler as described, for example, in U.S. Pat. No. 2,449,966, West German Pat. No. 2,024,186, Japanese Patent Application (OPI) Nos. 123625/74, 131448/74, and 42121/77, etc., a competing coupler as described, for example, in U.S. Pat. Nos. 3,876,428, 3,580,722, 2,998,314, 2,808,329, 2,742,832 and 2,689,793, etc., a stain preventing agent as described, for example, in U.S. Pat. Nos. 2,336,327, 2,728,659, 2,336,327, 2,403,721, 2,701,197 and 3,700,453, etc., a dye image stabilizing agent as described, for example, in British Pat. No. 1,326,889, U.S. Pat. Nos. 3,432,300, 3,698,909, 3,574,627, 3,573,050 and 3,764,337, etc., or the like.

The color photographic light-sensitive material produced according to the present invention can also contain conventional coupler(s) other than a magenta color forming coupler. A non-diffusible coupler which contains a hydrophobic group, called a ballast group, in the molecule thereof is preferred as a coupler. A coupler can have either a 4-equivalent or a 2-equivalent property with respect to the silver ion. In addition, a colored coupler providing a color correction effect, or a coupler which releases a development inhibitor upon a development can also be present therein. Furthermore, a coupler which provides a colorless product upon coupling can be employed.

A known open chain ketomethylene type coupler can be used as a yellow color forming coupler. Of these couplers, benzoyl acetanilide type and pivaloyl acetanilide type compounds are especially effective. Specific examples of yellow color forming couplers which can be employed are described, for example, in U.S. Pat. Nos. 2,875,057, 3,265,506, 3,408,194, 3,551,155, 3,582,322, 3,725,072 and 3,891,445, West German Pat. No. 1,547,868, West German Patent Application (OLS) Nos. 2,219,917, 2,261,361 and 2,414,006, British Pat. No. 1,425,020, Japanese Patent Publication No. 10783/76, Japanese Patent Application (OPI) Nos. 26133/72, 73147/73, 102636/76, 6341/75, 123342/75, 130442/75, 21827/76 and 87650/75, etc.

A phenol type compound, a naphthol type compound, etc., can be employed as a cyan color forming coupler. Specific examples of cyan color forming couplers which can be employed are those described, for example, in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, West German Patent Application (OLS) Nos. 2,414,830 and 2,454,329, Japanese Patent Application (OPI) Nos. 59838/73, 26034/76, 5055/73, 146828/76, 73050/80, etc.

Two or more kinds of the couplers described above can be incorporated into the same layer, or the same coupler compound can also be present in two or more layers.

A known method, for example, the method described in U.S. Pat. No. 2,322,027, can be used in order to incorporate the couplers described above into a silver halide emulsion layer. The coupler is dispersed in a hydrophilic colloid and then mixed with a silver halide emulsion. When a coupler having an acid group such as a carboxylic acid group, a sulfonic acid group, etc., is used, it can be incorporated into a hydrophilic colloid as an alkaline aqueous solution thereof.

The silver halide emulsions which can be used in the present invention are those wherein silver chloride, silver bromide, or a mixed silver halide such as silver chlorobromide, silver iodobromide, or silver chloroiodobromide is finely dispersed in a hydrophilic polymer such as gelatin. The silver halide can be chosen depending on the intended use of the photographic light-sensitive material from dispersions having a uniform grain size or those having a wide grain size distribution or from dispersions having an average grain size of from about 0.1 micron to 3 microns. These silver halide emulsions can be prepared, for example, by a single jet method, by a double jet method or a controlled double jet method, or by a ripening method such as an ammonia method, a neutral method, or an acid method. Also, these silver halide emulsions can be subjected to chemical sensitization such as a sulfur sensitization, a gold sensitization, a reduction sensitization, etc., and can contain a speed increasing agent such as a polyoxyethylene compound, an onium compound, etc. Further, a silver halide emulsion of the type wherein latent images are predominantly formed on the surface of the grains or of the type where latent images are predominantly formed inside the grains can be used in the present invention. Also, two or more kinds of silver halide photographic emulsions prepared separately and then mixed can be employed.

As a hydrophilic high molecular weight substance composed of the photographic light-sensitive layer of the present invention, a protein such as gelatin, etc., a high molecular weight non-electrolyte such as polyvinyl alcohol, polyvinyl pyrrolidone, polyacrylamide, etc., an acidic polymer such as an alginate, a polyacrylic acid salt, etc., a high molecular weight ampholite such as a polyacrylamide treated by the Hoffman rearrangement reaction, a copolymer of acrylic acid and N-vinylimidazole, etc., a cross-linking polymer as described in U.S. Pat. No. 4,215,195, and the like are suitable. Furthermore, a hydrophobic polymer dispersion such as a latex of polybutyl acrylate, etc., can be included in the continuous phase of such a hydrophilic high molecular weight substance.

The silver halide emulsion used in the present invention can be chemically sensitized, as noted above, using conventional methods. Examples of suitable chemical sensitizers include, for example, gold compounds such as chloroaurates and gold trichloride as described in U.S. Pat. Nos. 2,399,083, 2,540,085, 2,597,856, and 2,597,915; salts of a noble metal, such as platinum, palladium, iridium, rhodium and ruthenium, as described in U.S. Pat. Nos. 2,448,060, 2,540,086, 2,566,245, 2,566,263 and 2,598,079; sulfur compounds capable of forming silver sulfide by reacting with a silver salt, such as those described in U.S. Pat. Nos. 1,574,944, 2,410,689, 3,189,458 and 3,501,313; stannous salts, amines, and other reducing compounds such as those described in U.S. Pat. Nos. 2,487,850, 2,518,698, 2,521,925, 2,521,926, 2,694,637, 2,983,610 and 3,201,254 and the like.

Various compounds can be added to the photographic emulsions used in the present invention in order to prevent a reduction of the sensitivity or a formation of fog during preparation, storage, or processing. A wide variety of such compounds are known, such as heterocyclic compounds, mercury-containing compounds, mercapto compounds or metal salts, including 4-hydroxy-6-methyl-1,3,3a,7-tetraazaindene, 3-methylbenzothiazole and 1-phenyl-5-mercaptotetrazole. Other examples of such compounds which can be used are described, for example, in U.S. Pat. Nos. 1,758,576, 2,110,178, 2,131,038, 2,173,628, 2,697,040, 2,304,962, 2,324,123, 2,394,198, 2,444,605-8, 2,566,245, 2,694,716, 2,697,099, 2,708,162, 2,728,663-5, 2,476,536, 2,824,001, 2,843,491, 2,886,437, 3,052,544, 3,137,577, 3,220,839, 3,226,231, 3,236,652, 3,251,691, 3,252,799, 3,287,135, 3,326,681, 3,420,668 and 3,622,339, British Pat. Nos. 893,428, 403,789, 1,173,609 and 1,200,188, as well as in K. Mees, *The Theory of the Photographic Process*, 3rd Ed. (1966) and the literature references cited therein.

The photographic emulsion used in the present invention can also contain one or more surface active agents. These surface active agents are commonly used as a coating aid. However, in some cases they are used as an emulsifier, a dispersant, a sensitizer, an antistatic agent, or an adhesion preventing agent.

The surface active agents can be classified into various groups, as follows: natural surface active agents such as saponin; nonionic surface active agents such as alkylene oxides, glycerols and glycidols; cationic surface active agents such as higher alkylamines, quaternary ammonium salts, heterocyclic compounds such as pyridine and the like, phosphoniums or sulfoniums; anionic surface active agents containing an acid group such as a carboxylic acid group, a sulfonic acid group, a phosphoric acid group, a sulfuric acid ester group, or phosphoric acid ester group; amphoteric surface active agents such as aminoacids, aminosulfonic acids, aminoalcohol sulfuric acid esters or aminoalcohol phosphoric acid esters. Some examples of those surface active agents which can be used are described in U.S. Pat. Nos. 2,271,623, 2,240,472, 2,288,226, 2,739,891, 3,068,101, 3,158,484, 3,201,253, 3,210,191, 3,294,540, 3,415,649, 3,441,413, 3,442,654, 3,475,174, 3,545,974, West German Patent Application (OLS) No. 1,942,665, British Pat. Nos. 1,077,317 and 1,918,450, as well as Ryohei Oda et al., *Kaimenkasseizai no Gosei to Sono Oyo (Synthesis and Application of Surface Active Agents)*, Maki Shoten (1964), A. W. Perry, *Surface Active Agents*, Interscience Publications, Inc. (1958) and J. P. Sisley, *Encyclopedia of Surface Active Agents*, Vol. II, Chemical Publishing Co. (1964).

The photographic emulsions can be spectrally sensitized, or supersensitized, using a cyanine-type dye, such as a cyanine, merocyanine, carbocyanine, etc., individually, in combinations, or in combination with a styryl dye.

These spectral sensitization techniqus are well known, and are described, for example, in U.S. Pat. Nos. 2,688,545, 2,912,329, 3,397,060, 3,615,635 and 3,628,964, British Pat. Nos. 1,195,302, 1,242,588 and 1,293,862, West German Patent Application (OLS) Nos. 2,030,326 and 2,121,780, Japanese Patent Publication Nos. 4936/68 and 14030/69, etc. The sensitizers can be selected as desired depending on the purposes and use of the photographic materials to be sensitized.

The hydrophilic colloid layer, and in particular a gelatin layer in the photographic light-sensitive material used in the present invention, can be hardened using various kinds of cross-linking agents. For instance, an inorganic compound such as a chromium salt and a zirconium salt, or an aldehyde type cross-linking agent such as mucochloric acid, or 2-phenoxy-3-chloromalealdehydic acid as described in Japanese Patent Publication No. 1872/71 can be effectively used in the present invention. However, non-aldehyde type cross-linking agents such as compounds having plural epoxy rings as described in Japanese Patent Publication No. 7133/59, the poly(1-aziridinyl) compounds as described in Japanese Patent Publication No. 8790/62, the active halogen compounds as described in U.S. Pat. Nos. 3,362,827 and 3,325,287 and the vinyl sulfone compounds as described in U.S. Pat. Nos. 2,994,611 and 3,582,322, Belgian Pat. No. 686,440, etc., are particularly suitable for use in the photographic light-sensitive material of the present invention.

The silver halide photographic emulsion of the present invention is suitably applied to a support. Illustrative supports include rigid materials such as glass, metal and ceramics, and flexible materials and the type of support chosen depends on the end-use objects. Typical examples of flexible supports include a cellulose nitrate film, a cellulose acetate film, a polyvinyl acetal film, a polystyrene fulm, a polyethylene terephthalate film, a polycarbonate film and a laminate thereof, a baryta coated paper, a paper coated with an α-olefin polymer, such as polyethylene, polypropylene and an ethylene-butene copolymer, a plastic film having a roughened surface as described in Japanese Patent Publication No. 19068/72, and the like. Depending upon the end-use objects of the photographic light-sensitive material, the support can be transparent, colored by adding a dye or pigment, opaque by adding, for example, titanium white, or light-shielding by adding, for example, carbon black.

The layer of the photographic light-sensitive material can be coated on a support using various coating methods, including a dip coating method, an air-knife coating method, a curtain coating method, an extrusion coating method using a hopper as described in U.S. Pat. No. 2,681,294. Also two or more layers can be coated simultaneously, using methods as described in U.S. Pat. Nos. 2,761,791, 3,508,947, 2,941,898, 3,526,528, etc.

The present invention is applicable to not only the so-called multilayer type photographic light-sensitive material comprising a support having superimposed thereon emulsion layers, each of which is sensitive to radiation of a substantially different wavelength region and forms color images of a substantially different hue, but also the so-called mixed packet type photographic light-sensitive material comprising a support having coated thereon a layer containing packets which are sensitive to radiation of substantially different wavelength regions and form color images of a substantially different hue. The present invention can be applied to a color negative film, a color positive film, a color reversal film, a color printing paper, a color reversal printing paper, and the like.

The color photographic light-sensitive material of the present invention is, after exposure, subjected to a development processing to form dye images. Development processing includes basically a color development step, a bleaching step and a fixing step. Each step can be carried out individually or two or more steps can be combined as one step where a processing solution having two or more functions is used. Also, each step can be separated into two or more steps. The development processing can further include a pre-hardening step, a neutralization step, a first development (black-and-white development) step, a stabilizing step, a water washing step, and the like, if desired. The temperature of processing can be varied depending on the photographic light-sensitive material, the processing method, and the like. In general, the processing steps are carried out at a temperature from 18° C. to 60° C. These steps need not necessarily be conducted at the same temperature.

A color developer solution is an alkaline solution having a pH of more than 8, preferably from 9 to 12, and containing, as a developing agent, a compound whose oxidation product is capable of forming a colored compound when reacted with a color forming agent, i.e., a color coupler. The developing agent described above includes a compound capable of developing an exposed silver halide and having a primary amino group on an aromatic ring, and a precursor which forms such compound. Typical examples of preferred developing agents are, for example, 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-dimethylaniline, 4-amino-3-methoxy-N,N-diethylaniline, 4-amino-3-methyl-N-ethyl-N-β-ethoxyethylaniline, 4-amino-3-methoxy-N-ethyl-N-β-methoxyethylaniline, 4-amino-3-β-methanesulfonamidoethyl-N,N-diethylaniline, and the salts thereof (for example, the sulfates, the hydrochlorides, the sulfites, the p-toluene sulfonates, and the like). Other developing agents such as those described in U.S. Pat. Nos. 2,193,015 and 2,592,364, Japanese Patent Application (OPI) No. 64933/73, L. F. A. Mason, *Photographic Processing Chemistry*, pages 226-229, Focal Press, London (1966), T. H. James, *The Theory of the Photographic Process*, 4th Edition, pages 315-320, Macmillan, New York (1977), etc., can be used. Further, an aminophenol as described in T. H. James, *The Theory of the Photographic Process*, 4th Edition, pages 311-315, etc., can be used. Also, a 3-pyrazolidone developing agent can be used together with these developing agents.

The color developer solution can optionally contain various additives. Typical examples of such additives include alkaline agents (for example, alkali metal or ammonium hydroxides, carbonates or phosphates); pH-adjusting agents or buffers (for example, weak acids such as acetic acid, boric acid, etc., weak bases, or salts thereof); developing accelerators (for example, various pyridinium compounds or cationic compounds such as those described in U.S. Pat. Nos. 2,648,604 and 3,671,247; potassium nitrate; sodium nitrate; condensation products of polyethylene glycol, and their derivatives such as those described in U.S. Pat. Nos. 2,533,990, 2,577,127 and 2,950,970; nonionic compounds such as polythioethers represented by those described in British Pat. Nos. 1,020,033 and 1,020,032; polymeric compounds having sulfite ester groups such as those described in U.S. Pat. No. 3,068,097; organic amines such as pyridine and ethanolamine; benzyl alcohol; hydrazines and the like); anti-fogging agents (for example, alkali metal bromides; alkali metal iodides; nitrobenzimidazoles such as those described in U.S. Pat. Nos. 2,496,940 and 2,656,271; mercaptobenzimidazole; 5-methylbenztriazole; 1-phenyl-5-mercaptotetrazole; compounds for use in rapid processing such as those described in U.S. Pat. Nos. 3,113,864, 3,342,596, 3,295,976, 3,615,522 and 3,597,199; thiosulfonyl compounds such as those described in British Pat. No. 972,211; phenazine-N-oxides such as those described in Japanese Patent Publication No. 41675/71; those described in *Kagaku Shashin Binran* (*Manual of Scientific Photography*), Vol. II, pages 29-47, and the like); stain or sludge preventing agents such as those described in U.S. Pat. Nos. 3,161,513 and 3,161,514, and British Pat. Nos. 1,030,442, 1,144,481 and 1,251,558; interlayer-effect accelerators disclosed in U.S. Pat. No. 3,536,487; preservatives (for example, sulfites, bisulfites, hydroxyamine hydrochloride, formsulfite, alkanolaminesulfite adducts, etc.) and the like.

The color photographic light-sensitive material of the present invention can be treated with various solutions prior to color development.

In the case of color reversal films, treatment with a first development solution is also carried out prior to the color development. As the first development solution, an alkaline aqueous solution containing at least one developing agent, such as hydroquinone, 1-phenyl-3-pyrazolidone, N-methyl-p-aminophenol and the like can be employed. The solution can also contain inorganic salts such as sodium sulfate; pH-adjusting agents or buffers such as borax, boric acid, sodium hydroxide and sodium carbonate; development fog inhibitors such as alkali metal halides (such as potassium bromide, etc.), and the like.

The additives illustrated above and the amounts thereof employed are well known in the color processing field.

After color development, the color photographic materials are usually bleached and fixed. The processes can be effected in a blix bath which combines the bleaching and fixing steps. Various compounds can be used as a bleaching agent, for example, ferricyanides, dichromates; water-soluble iorn (III) salts, water-soluble cobalt (III) salts; water-soluble copper (II) salts; water-soluble quinones; nitrosophenols; complex salts of a polyvalent cation such as iron (III), cobalt (III), copper (II), etc., and an organic acid, for example, metal complex of an aminopolycarboxylic acid such as ethylenediaminetetraacetic acid, nitrilotriacetic acid, iminodiacetic acid, N-hydroxyethylethylenediaminetriacetic acid, etc., malonic acid, tartaric acid, malic acid, diglycolic acid and dithioglycolic acid, and copper complex salt of 2,6-dipicolinic acid; peracids such as alkylperacids, persulfates, permanganates and hydrogen peroxide; hypochlorites; chlorine; bromine; bleaching powder; and the like. These can be suitably used, individually or in combination. To the bleaching solution, bleaching accelerators such as those described in U.S. Pat. Nos. 3,042,520 and 3,241,966, Japanese Patent Publication Nos. 8506/70 and 8836/70 and various other additives can be added.

Any known fixing solution can be used for fixing the photographic materials of the present invention. That is, ammonium, sodium, or potassium thiosulfate can be used as a fixing agent at a concentration of about 50 to about 200 g/liter. Fixing solutions can further contain stabilizers such as sulfites and metabisulfites; hardeners such as potassium alum; pH buffers such as acetates and borates, and the like. The fixing solution generally has a pH of more than 3 or less.

Bleaching baths, fixing baths and blixing baths as described, for example, in U.S. Pat. No. 3,582,322, Japanese Patent Application (OPI) No. 101934/73, West German Pat. No. 1,051,117 can also be employed.

The present invention will be explained in greater detail with reference to the following examples, but the present invention should not be construed as being limited thereto.

EXAMPLE 1

A latex solution containing $5.6 \times 10^{-3}$ mol of each of the 4-equivalent magenta polymer coupler latexes (A), (K) and (B) according to the present invention and the comparative 4-equivalent magenta polymer coupler latexes (I), (II), (III), (IV) and (V) described below which were prepared by the synthesis method I and 30 ml of water were mixed with 100 g of a silver halide emulsion containing $5.6 \times 10^{-2}$ mol of silver iodobromide and 8 g of gelatin, and to the mixture was added 8 ml of a 4% acetone solution of 2-hydroxy-4,6-dichloro-s-triazine sodium salt. After adjusting the pH to 6.5, the emulsion was coated on a cellulose triacetate support having a subbing layer to prepare Samples 1 to 8.

These films were exposed stepwise for sensitometry and then subjected to the following color development processing.

| Color Development Processing Step | Time | Temperature (°C.) |
| --- | --- | --- |
| 1. Color development | 3 min 15 sec | 38 |
| 2. Bleaching | 6 min 30 sec | " |
| 3. Washing with water | 2 min | " |
| 4. Fixing | 4 min | " |
| 5. Washing with water | 4 min | " |

| Color Development Processing Step | Time | Temperature (°C.) |
|---|---|---|
| 6. Stabilizing | 1 min | " |

The processing solutions used in the color development processing had the following compositions:

| Color Developer Solution | |
|---|---|
| Water | 800 ml |
| 4-(N—Ethyl-N—hydroxyethyl)amino-2-methylaniline Sulfate | 5 g |
| Sodium Sulfite | .5 g |
| Hydroxylamine Sulfate | 2 g |
| Potassium Carbonate | 30 g |
| Potassium Hydrogencarbonate | 1.2 g |
| Potassium Bromide | 1.2 g |
| Sodium Chloride | 0.2 g |
| Trisodium Nitrilotriacetate | 1.2 g |
| Water to make | 1 l |
| | (pH 10.1) |

| Bleaching Solution | |
|---|---|
| Water | 800 ml |
| Iron (III) Ammonium Ethylenediaminetetraacetate | 100 g |
| Disodium Ethylenediaminetetraacetate | 10 g |
| Potassium Bromide | 150 g |
| Acetic Acid | 10 g |
| Water to make | 1 l |
| | (pH 6.0) |

| Fixing Solution | |
|---|---|
| Water | 800 ml |
| Ammonium Thiosulfate | 150 g |
| Sodium Sulfite | 10 g |
| Sodium Hydrogensulfite | 2.5 g |
| Water to make | 1 l |
| | (pH 6.0) |

| Stabilizing Bath | |
|---|---|
| Water | 800 ml |
| Formalin (37 wt % formaldehyde) | 5 ml |
| Fuji Driwell | 3 ml |
| Water to make | 1 l |

The photographic properties thus-obtained are shown in Table 1 below.

TABLE 1

| Sample | Latex Used | Fog | Gamma | Relative[*1] Sensitivity | Maximum Color Density |
|---|---|---|---|---|---|
| 1. (Present Invention) | (A) | 0.05 | 1.40 | 100 | 1.40 |
| 2. (Present Invention) | (K) | 0.05 | 1.35 | 99 | 1.40 |
| 3. (Present Invention) | (B) | 0.05 | 1.32 | 97 | 1.40 |
| 4. (Comparison) | (I) | 0.07 | 1.25 | 73 | 0.85 |
| 5. (Comparison) | (II) | 0.05 | 1.17 | 75 | 1.15 |
| 6. (Comparison) | (III) | 0.05 | 0.90 | 65 | 1.01 |
| 7. (Comparison) | (IV) | 0.05 | 0.60 | 56 | 0.84 |
| 8. (Comparison) | (V) | 0.05 | 0.55 | 45 | 0.40 |

[*1]Relative value of a reciprocal of the exposure amount required for obtaining an optical density of fog value + 0.2.

It is apparent from the results shown in Table 1 that Samples 1, 2 and 3 according to the present invention provide increased gamma, relative sensitivity, and maximum color density without an increase in fog in comparison with the Comparative Samples 4, 5, 6, 7 and 8, and thus they are clearly advantageous with respect to the color forming property.

The comparative 4-equivalent magenta polymer coupler latexes (I), (II), (III), (IV) and (V) have the following compositions.

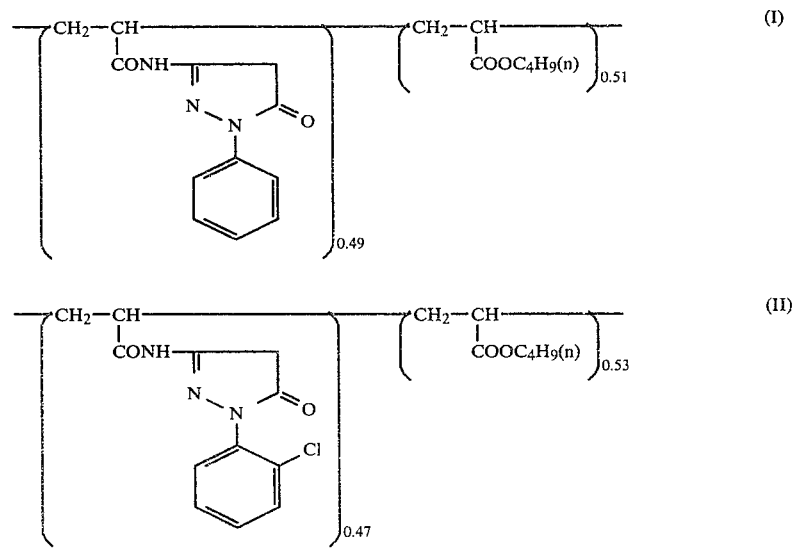

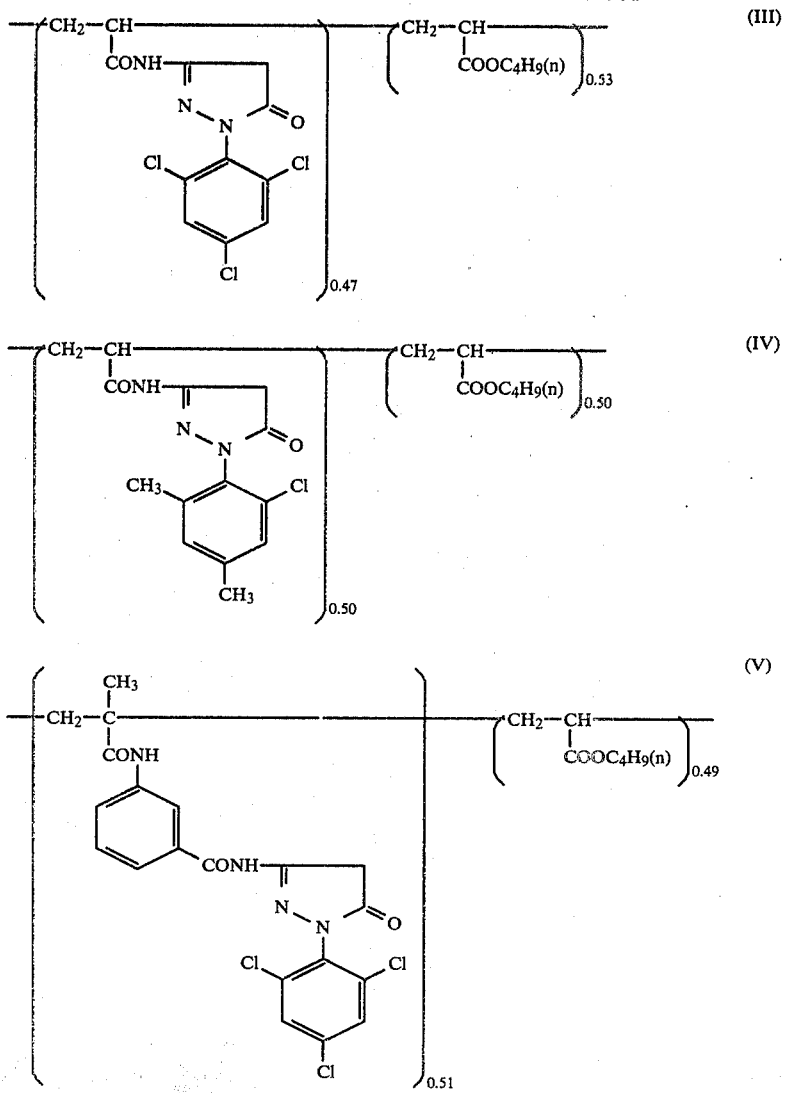

EXAMPLE 2

A latex aqueous solution containing $7.5 \times 10^{-3}$ mol of each of the 4-equivalent magenta polymer coupler latexes (E), (N), (V) and (B) according to the present invention and the comparative magenta polymer coupler latexes (VI), (VII), (VIII) and (IX) described below which were prepared by the synthesis method I and 40 ml of water were mixed with 100 g of a silver halide emulsion containing $8.4 \times 10^{-2}$ mol of silver iodobromide and 10 g of gelatin, to which 8 ml of a 4% acetone solution of 2-hydroxy-4,6-dichloro-s-triazine sodium salt was added. The pH of the mixture was adjusted to 6.7 and the mixture was coated on a cellulose triacetate film in an amount of silver coated of $1.2 \times 10^{-3}$ mol/m², to prepare Samples 9, 10, 11, 12, 13, 14, 15 and 16.

These films were exposed stepwise for sensitometry and then subjected to the following color development processing.

| Color Development Processing Step (38° C.) | |
|---|---|
| | Time (min) |
| 1. First development | 3 |
| 2. Washing with water | 1 |
| 3. Reversal | 2 |
| 4. Color development | 6 |
| 5. Control | 2 |
| 6. Bleaching | 6 |
| 7. Fixing | 4 |
| 8. Washing with water | 4 |
| 9. Stabilizing | 1 |
| 10. Drying | |

The processing solutions used in the color development processing had the following compositions:

| First Development Solution | |
|---|---|
| Water | 800 ml |
| Sodium Tetrapolyphosphate | 2.0 g |
| Sodium Hydrogensulfite | 8.0 g |
| Sodium Sulfite | 37.0 g |
| 1-Phenyl-3-pyrazolidone | 0.35 g |

| -continued | |
|---|---|
| First Development Solution | |
| Hydroquinone | 5.5 g |
| Sodium Carbonate Monohydrate | 28.0 g |
| Potassium Bromide | 1.5 g |
| Potassium Iodide | 13.0 mg |
| Sodium Thiocyanate | 1.4 g |
| Water to make | 1 l |

| Reversal Solution | |
|---|---|
| Water | 800 ml |
| Hexasodium Nitrilo-N,N,N—trimethylene Phosphonate | 3.0 g |
| Stannous Chloride Dihydrate | 1.0 g |
| Sodium Hydroxide | 8.0 g |
| Glacial Acetic Acid | 15.0 ml |
| Water to make | 1 l |

| Color Development Solution | |
|---|---|
| Water | 800 ml |
| Sodium Tetrapolyphosphate | 2.0 g |
| Benzyl Alcohol | 5.0 ml |
| Sodium Sulfite | 7.5 g |
| Trisodium Phosphate (12 hydrate) | 36.0 g |
| Potassium Bromide | 1.0 g |
| Potassium Iodide | 90.0 mg |
| Sdoium Hydroxide | 3.0 g |
| Citrazic Acid | 1.5 g |
| 4-Amino-3-methyl-N—ethyl-N—($\beta$-hydroxyethyl)aniline Sesquisulfate Monohydrate | 11.0 g |
| Ethylenediamine | 3.0 g |
| Water to make | 1.0 l |

| Control Solution | |
|---|---|
| Water | 800 ml |
| Glacial Acetic Acid | 5.0 ml |
| Sodium Hydroxide | 3.0 g |
| Dimethylaminoethaneisothiourea Dihydrochloride | 1.0 g |
| Water to make | 1 l |

| Bleaching Solution | |
|---|---|
| Water | 800 ml |
| Sodium Ethylenediaminetetraacetate Dihydrate | 2.0 g |
| Ammonium Iron (II) Ethylenediaminetetraacetate Dihydrate | 120.0 g |
| Potassium Bromide | 100.0 g |
| Water to make | 1 l |

| Fixing Solution | |
|---|---|
| Water | 800 ml |
| Ammonium Thiosulfate | 80.0 g |
| Sodium Sulfite | 5.0 g |
| Sodium Hydrogensulfite | 5.0 g |
| Water to make | 1 l |

| Stabilizing Bath | |
|---|---|
| Water | 800 ml |
| Formalin (37 wt % formaldehyde) | 5.0 ml |
| Fuji Driwell | 5.0 ml |

| -continued | |
|---|---|
| Stabilizing Bath | |
| Water to make | 1.0 l |

The photographic properties thus-obtained are shown in Table 2 below.

TABLE 2

| Sample | Latex Used | Fog | Gamma | Maximum Color Density |
|---|---|---|---|---|
| 9. (Present Invention) | (E) | 0.03 | 1.50 | 1.50 |
| 10. (Present Invention) | (N) | 0.03 | 1.53 | 1.55 |
| 11. (Present Invention) | (V) | 0.03 | 1.60 | 1.55 |
| 12. (Present Invention) | (B) | 0.03 | 1.49 | 1.50 |
| 13. (Comparison) | (VI) | 0.03 | 0.85 | 1.10 |
| 14. (Comparison) | (VII) | 0.03 | 0.72 | 0.86 |
| 15. (Comparison) | (VIII) | 0.02 | 0.60 | 0.70 |
| 16. (Comparison) | (IX) | 0.03 | 0.75 | 0.92 |

It is apparent from the results shown in Table 2 that Samples 9, 10, 11 and 12 according to the present invention provide increased gamma, relative sensitivity, and maximum color density without an increase in fog in comparison with the Comparative Samples 13, 14, 15 and 16, and thus they are clearly advantageous with respect to the color forming property.

The comparative 4-equivalent magenta polymer coupler latexes (VI), (VII), (VIII) and (IX) have the following compositions.

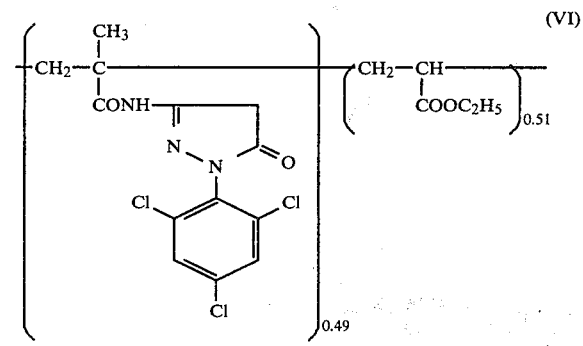

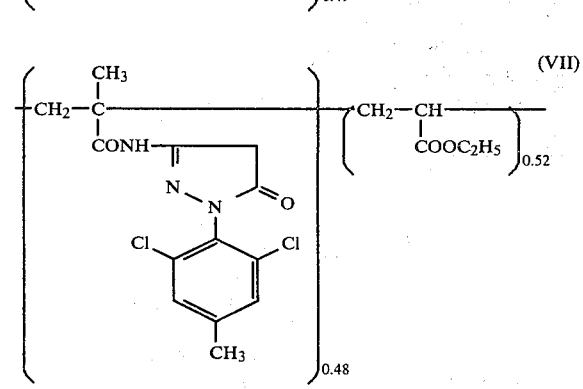

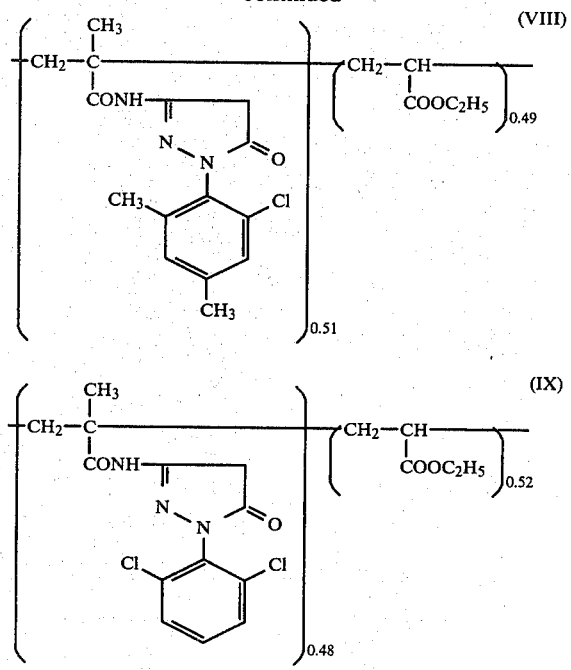

EXAMPLE 3

$5.6 \times 10^{-3}$ mol of each of the 4-equivalent magenta polymer coupler latexes (A'), (B') and (C') according to the present invention and the comparative magenta polymer coupler latexes (X), (XI) and (XII) described below which were prepared by the synthesis method II and 30 ml of water were mixed with 100 g of a silver halide emulsion containing $5.6 \times 10^{-2}$ mol of silver iodobromide and 8 g of gelatin, and to the mixture was added 8 ml of a 4% acetone solution of 2-hydroxy-4,6-dichloro-s-triazine sodium salt. After adjusting the pH to 6.5, the emulsion was coated on a cellulose triacetate support having a subbing layer to prepare Samples 17 to 22.

These films were exposed stepwise for sensitometry and then subjected to the following color development processing.

| Color Development Processing Step | Time | Temperature (°C.) |
|---|---|---|
| 1. Color development | 3 min 15 sec | 38 |
| 2. Bleaching | 6 min 30 sec | " |
| 3. Washing with water | 2 min | " |
| 4. Fixing | 4 min | " |
| 5. Washing with water | 4 min | " |
| 6. Stabilizing | 1 min | " |

The processing solutions used in the color development processing had the following compositions.

| Color Developer Solution | |
|---|---|
| Water | 800 ml |
| 4-(N—Ethyl-N—hydroxyethyl)amino-2-methylaniline Sulfate | 5 g |
| Sodium Sulfite | 5 g |
| Hydroxylamine Sulfate | 2 g |
| Potassium Carbonate | 30 g |
| Potassium Hydrogencarbonate | 1.2 g |
| Potassium Bromide | 1.2 g |

| Color Developer Solution | |
|---|---|
| Sodium Chloride | 0.2 g |
| Trisodium Nitrilotriacetate | 1.2 g |
| Water to make | 1 l |
| | (pH 10.1) |

| Bleaching Solution | |
|---|---|
| Water | 800 ml |
| Iron (III) Ammonium Ethylenediaminetetraacetate | 100 g |
| Disodium Ethylenediaminetetraacetate | 10 g |
| Potassium Bromide | 150 g |
| Acetic Acid | 10 g |
| Water to make | 1 l |
| | (pH 6.0) |

| Fixing Solution | |
|---|---|
| Water | 800 ml |
| Ammonium Thiosulfate | 150 g |
| Sodium Sulfite | 10 g |
| Sodium Hydrogensulfite | 2.5 g |
| Water to make | 1 l |
| | (pH 6.0) |

| Stabilizing Bath | |
|---|---|
| Water | 800 ml |
| Formalin (37 wt % formaldehyde) | 5 ml |
| Driwell | 3 ml |
| Water to make | 1 l |

The photographic properties thus-obtained are shown in Table 3 below.

TABLE 3

| Sample | Latex Used | Fog | Gamma | Relative[*1] Sensitivity | Maximum Color Density |
|---|---|---|---|---|---|
| 17. (Present Invention) | (A') | 0.05 | 1.30 | 100 | 1.35 |
| 18. (Present Invention) | (B') | 0.05 | 1.17 | 95 | 1.33 |
| 19. (Present Invention) | (G') | 0.05 | 1.29 | 97 | 1.35 |
| 20. (Comparison) | (X) | 0.05 | 0.75 | 65 | 0.97 |
| 21. (Comparison) | (XI) | 0.05 | 0.82 | 70 | 1.03 |
| 22. (Comparison) | (XII) | 0.05 | 0.65 | 50 | 0.75 |

[*1]Relative value of a reciprocal of the exposure amount required for obtaining an optical density of fog value + 0.2.

It is apparent from the results shown in Table 3 that Samples 17, 18 and 19 according to the present invention provide increased gamma, relative sensitivity, and maximum color density without an increase in fog in comparison with the Comparative Samples 20, 21 and 22, and thus they are clearly advantageous with respect to the color forming property.

The comparative 4-equivalent magenta polymer coupler latexes (X), (XI) and (XII) have the following compositions.

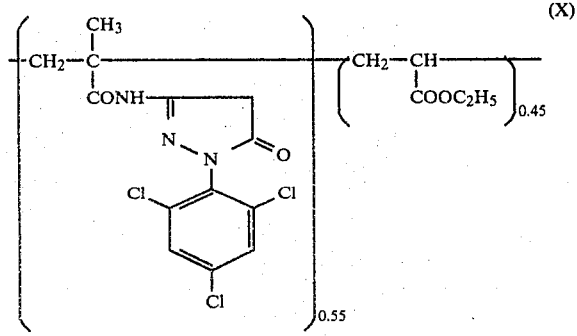

(X)

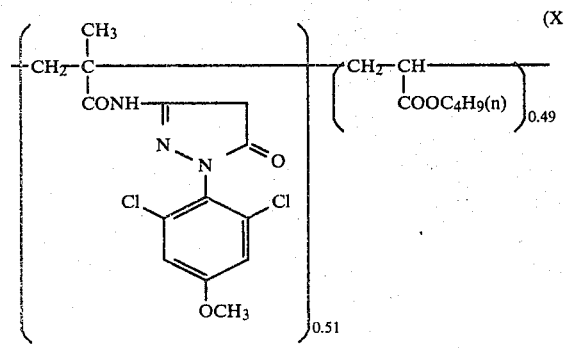

(XI)

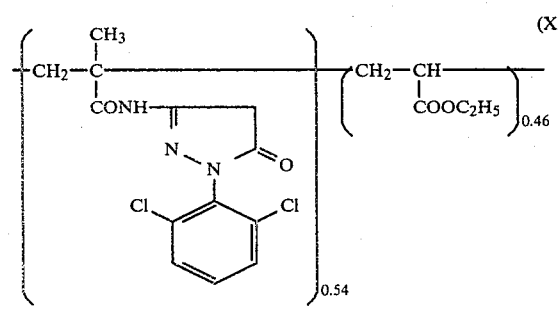

(XII)

EXAMPLE 4

Samples 23 to 28 having a silver halide emulsion layer containing each of the magenta polymer coupler latexes (E), (J) and (V) according to the present invention and the comparative magenta polymer coupler latexes (XIII), (XIV) and (XV) described below which were prepared by the synthesis method I were prepared in the same manner as described in Example 1. These samples were uniformly exposed to light so as to provide a color density between 0.48 and 0.52 and then subjected to the same color development processing as described in Example 1. The transparent visible spectral absorption characteristics of the films thus processed were measured using a spectral densitometer. The results obtained are shown in Table 4.

TABLE 4

| Sample | Latex Used | Cyan(*1) Color Turbidity (%) | Yellow(*2) Color Turbidity (%) | Maximum Absorption Wavelength (nm) | S(*3) |
|---|---|---|---|---|---|
| 23 (Present Invention) | (E) | 9 | 20 | 542 | 30 |
| 24 (Present Invention) | (J) | 11 | 21 | 540 | 41 |
| 25 (Present Invention) | (V) | 10 | 20 | 543 | 35 |
| 26 (Comparison) | (XIII) | 15 | 25 | 530 | 53 |
| 27 (Comparison) | (XIV) | 14 | 24 | 538 | 54 |
| 28 (Comparison) | (XV) | 15 | 26 | 534 | 55 |

(*1)Ratio of an absorptivity at 620 nm (cyan color) to an absorptivity at 550 nm (magenta color)

(*2)Ratio of an absorptivity at 430 nm (yellow color) to an absorptivity at 550 nm (magenta color)

$$(*3)S = \frac{\text{Absorptivity at } [\lambda max + 60]nm}{\text{Absorptivity at } \lambda max} \times 100$$

In view of the color reproduction, the smaller the color turbidity and S values, the more desirable the spectral absorption characteristics. It is apparent from the results shown in Table 4 that the samples according to the present invention provide smaller color turbidity and S values in comparison with the comparative samples in spite of the fact that they have a maximum absorption at a longer wavelength range, and thus they have improved spectral absorption characteristics.

The comparative 4-equivalent magenta polymer coupler latexes (XIII), (XIV) and (XV) have the following compositions.

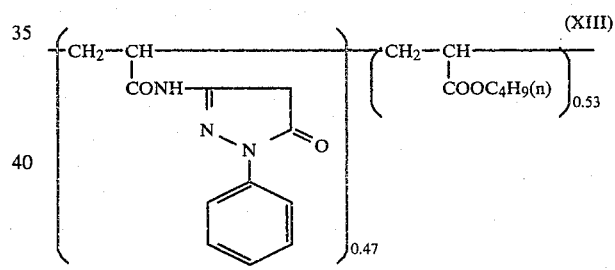

(XIII)

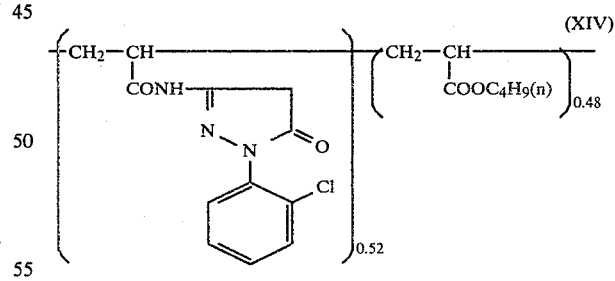

(XIV)

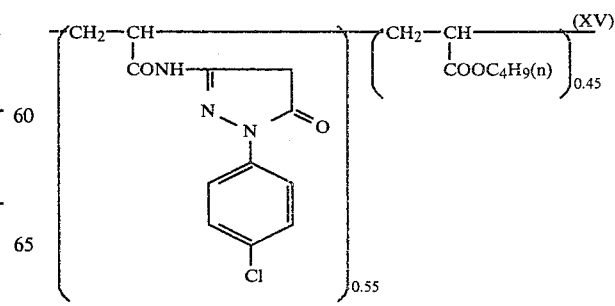

(XV)

EXAMPLE 5

Samples 29 to 39 having a silver halide emulsion layer containing each of the magenta polymer coupler latexes (B), (E), (P), (J), (V), (A'), (F') and (B') according to the present invention and the comparative magenta polymer coupler latexes (XIII), (XIV) and (XV) described in Example 4 which were prepared by the synthesis method I were prepared in the same manner as described in Example 2. These samples were uniformly exposed to light so as to provide a color density between 0.48 and 0.52 and then subjected to the same color development processing as described in Example 2. The transparent visible spectral absorption characteristics of the films thus-processed were measured using a spectral densitometer. The results obtained are shown in Table 5.

TABLE 5

| Sample | Latex Used | Cyan[*1] Color Turbidity (%) | Yellow[*2] Color Turbidity (%) | Maximum Absorption Wavelength (nm) | S[*3] |
|---|---|---|---|---|---|
| 29 (Present Invention) | (B) | 15 | 15 | 543 | 25 |
| 30 (Present Invention) | (E) | 18 | 17 | 542 | 27 |
| 31 (Present Invention) | (P) | 18 | 17 | 542 | 27 |
| 32 (Present Invention) | (J) | 21 | 24 | 544 | 39 |
| 33 (Present Invention) | (V) | 20 | 20 | 544 | 33 |
| 34 (Present Invention) | (A') | 17 | 17 | 543 | 27 |
| 35 (Present Invention) | (F') | 18 | 19 | 543 | 28 |
| 36 (Present Invention) | (B') | 19 | 20 | 548 | 34 |
| 37 (Comparison) | (XIII) | 30 | 29 | 531 | 45 |
| 38 (Comparison) | (XIV) | 29 | 28 | 538 | 50 |
| 39 (Comparison) | (XV) | 29 | 27 | 535 | 51 |

[*1] Ratio of an absorptivity at 620 nm (cyan color) to an absorptivity at 550 nm (magenta color)
[*2] Ratio of an absorptivity at 430 nm (yellow color) to an absorptivity at 550 nm (magenta color)

[*3] $S = \dfrac{\text{Absorptivity at } [\lambda_{max} + 60] \text{nm}}{\text{Absorptivity at } \lambda_{max}} \times 100$ In view of the color reproduction, the smaller the color turbidity and S values, the more desirable the spectral absorption characteristics. It is apparent from the results shown in Table 5 that samples according to the present invention provide smaller color turbidity and S values in comparison with the comparative samples in spite of they have the maximum absorption at a longer wavelength range, and thus they have the improved spectral absorption characteristics.

While the invention has been described in detail and with reference to specific embodiments thereof, it will be apparent to one skilled in the art that various changes and modifications can be made therein without departing from the spirit and scope thereof.

What is claimed is:

1. A silver halide color photographic light-sensitive material comprising a support having thereon a silver halide emulsion layer containing a magenta color image forming polymer coupler latex which is capable of forming a dye upon coupling with an oxidation product of an aromatic primary amine developing agent and which is a polymer or copolymer having a repeating unit derived from a monomer represented by the following general formula (I)

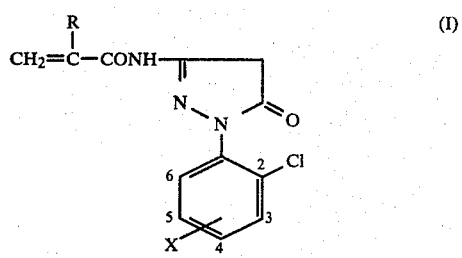

wherein R represents a hydrogen atom, a lower alkyl group containing from 1 to 4 carbon atoms or a chlorine atom; and X represents a halogen atom, an acylamino group, a carbamoyl group, a sulfonamido group, a sulfamoyl group, a cyano group or an alkoxycarbonyl group and which is present at the 4-position or 5-position of the phenyl group.

2. A silver halide color photographic light-sensitive material as claimed in claim 1, wherein R is a hydrogen atom.

3. A silver halide color photographic light-sensitive material as claimed in claim 1, wherein R is a methyl group.

4. A silver halide color photographic light-sensitive material as claimed in claim 1, wherein X is fluorine, chlorine or bromine.

5. A silver halide color photographic light-sensitive material as claimed in claim 1, wherein X is a fluorine atom, a chlorine atom, a bromine atom, an acetylamino group, a methylcarbamoyl group, a dimethylcarbamoyl group, a methanesulfonamido group, an ethylsulfamoyl group, a dimethylsulfamoyl group, a cyano group, a methoxycarbonyl group or an ethoxycarbonyl group.

6. A silver halide color photographic light-sensitive material as claimed in claim 1, wherein the polymer is a homopolymer.

7. A silver halide color photographic light-sensitive material as claimed in claim 1, wherein the polymer is a copolymer.

8. A silver halide color photographic light-sensitive material as claimed in claim 7, wherein the copolymer contains a repeating unit derived from a non-color forming monomer which does not couple with the oxidation product of an aromatic primary amine developing agent.

9. A silver halide color photographic light-sensitive material as claimed in claim 8, wherein the non-color forming monomer is an acrylic acid ester, an acrylic acid amide, a vinyl ester, an acrylonitrile, an aromatic vinyl compound, itaconic acid, citraconic acid, crotonic acid, vinylidene chloride, a vinyl alkyl ether, an ester of maleic acid, N-vinyl-2-pyrrolidone, N-vinyl pyridine, or 2- or 4-vinyl pyridine.

10. A silver halide color photographic light-sensitive material as claimed in claim 8, wherein the non-color forming monomer is an acrylic acid ester, a methacrylic acid ester or a maleic acid ester.

11. A silver halide color photographic light-sensitive material as claimed in claim 1, wherein the amount of the color forming portion in the polymer latex is from 5% to 80% by weight.

12. A silver halide color photographic light-sensitive material as claimed in claim 1, wherein the amount of the color forming portion in the polymer latex is from 20% to 70% by weight.

13. A silver halide color photographic light-sensitive material as claimed in claim 11, wherein the gram number of the polymer latex containing 1 mol of coupler monomer is from 250 to 3,000.

14. A silver halide color photographic light-sensitive material as claimed in claim 1, wherein the silver halide emulsion layer containing a magenta color image forming polymer coupler latex is a green-sensitive silver halide emulsion layer.

15. A silver halide color photographic light-sensitive material as claimed in claim 1, wherein the photographic light-sensitive material further comprises a blue-sensitive silver halide emulsion layer containing a yellow color image forming coupler and a red-sensitive silver halide emulsion layer containing a cyan color image forming coupler.

16. A method of forming a color image comprising developing an imagewise exposed silver halide color photographic light-sensitive material comprising a support having thereon a silver halide emulsion layer containing a magenta color image forming polymer coupler latex which is capable of forming a dye upon coupling with an oxidation product of an aromatic primary amine developing agent and which is a polymer or copolymer having a repeating unit derived from a monomer represented by the following general formula (I)

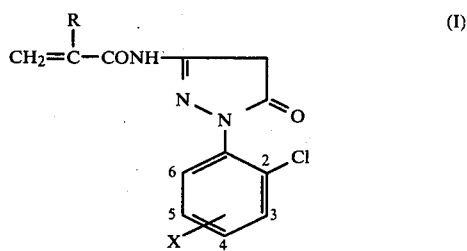

wherein R represents a hydrogen atom, a lower alkyl group containing from 1 to 4 carbon atoms or a chlorine atom; and X represents a halogen atom, an acylamino group, a carbamoyl group, a sulfonyl group, a sulfonamido group, a sulfamoyl group, a cyano group, or an alkoxycarbonyl group and which is present at the 4-position or 5-position of the phenyl group; wherein said developing is conducted using an alkaline aqueous solution containing an aromatic primary amine developing agent.

* * * * *